United States Patent [19]
Zaleski et al.

[11] Patent Number: 4,897,079
[45] Date of Patent: Jan. 30, 1990

[54] POLYMERIC SLEEVE FOR SURGICAL INSTRUMENTS

[75] Inventors: Edward R. Zaleski, Santa Ana; F. Richard Christ, Orange; Jacob F. R. Louw, El Toro, all of Calif.

[73] Assignee: Allergan, Inc., Irvine, Calif.

[21] Appl. No.: 222,938

[22] Filed: Jul. 22, 1988

[51] Int. Cl.$^4$ .................. A61B 17/20; A61M 7/00
[52] U.S. Cl. ........................... 604/22; 604/43; 604/167
[58] Field of Search ............ 604/22, 43, 167, 264, 604/294; 128/303 R, 305

[56] References Cited

U.S. PATENT DOCUMENTS

| | | |
|---|---|---|
| Re. 30,536 | 3/1981 | Perdreaux, Jr. . |
| 3,693,613 | 9/1972 | Kelman . |
| 3,805,787 | 4/1974 | Banko . |
| 3,945,375 | 3/1976 | Banko . |
| 4,014,333 | 3/1977 | McIntyre ........................ 604/43 |
| 4,417,578 | 11/1983 | Banko . |
| 4,428,748 | 1/1984 | Peyman et al. . |
| 4,504,264 | 3/1985 | Kelman . |
| 4,515,583 | 5/1985 | Sorich . |
| 4,573,979 | 3/1986 | Blake ........................ 604/43 |
| 4,681,561 | 7/1987 | Hood et al. . |
| 4,787,889 | 11/1988 | Steppe et al. ................. 604/22 |

*Primary Examiner*—Stephen C. Pellegrino
*Attorney, Agent, or Firm*—Gordon L. Peterson; Frank J. Uxa, Jr.

[57] ABSTRACT

A sleeve useful on a surgical instrument, in particular an instrument for treating the eye such as a vitrectomy cutter, is disclosed. Such sleeve includes a hollow elongated sleeve portion with at least one fluid outlet at or near its distal end portion, and a hub secured to the sleeve portion and adapted to receive at least a portion of the surgical instrument. The present sleeve is made of one or more organic polymeric materials and provides substantial benefits, e.g., providing effective fluid seals and being non-irrigating in use, and being disposable after use.

32 Claims, 2 Drawing Sheets

POLYMERIC SLEEVE FOR SURGICAL INSTRUMENTS

BACKGROUND OF THE INVENTION

This invention relates to sleeves useful on surgical instruments. More particularly, it relates to such sleeves which provide a path for fluid, such as irrigation fluid, to the eye during eye surgery.

Sleeves are currently used in conjunction with surgical instruments, such as vitrectomy cutters, irrigation-/aspiration instruments, emulsification instruments and the like, for example, to provide fluid to the eye, e.g., for irrigation and/or other purposes, while the eye is being surgically treated. Often, these sleeves are made of metal, such as stainless steel, in combination with silicone seals and tubes to connect irrigation infusion lines which support a fluidic-path to the eye during surgery. However, such metal sleeves must be very precisely and carefully made, for example, in order to avoid having the fluid leak from the fluidic path. If effective seals are not provided, fluid will leak proximally of the sleeve and/or through the opening through which the distal end portion of the instrument extends out of the sleeve. If the sleeve is made of metal, it must be precision machined to effect the desired fluid seals. In certain instances, the metal sleeve is custom built for one particular instrument so that the fluid seals are effective. Thus, the metal sleeves are expensive and difficult to produce, and may be useful with only one instrument, i.e., are often not interchangeable from instrument to instrument.

One alternative to metal which has been proposed is to make the sleeve out of a silicone polymer. Such silicone sleeves do often provide effective fluid seals. However, such sleeves, because of the softness of the silicone polymer, tend to collapse around the instrument, thus partially or completely blocking or obstructing the fluid flow path through the sleeve. This, in turn, is very disruptive to the surgical procedure and may be dangerous to the eyesight of the patient being treated. Also, such silicone sleeves are often tacky and can disadvantageously hang up or stick on the edge of the surgical incision.

Blake U.S. Pat. No. 4,573,979 discloses an irrigation-/aspiration device which includes a cannula made of a stiff material such as metal or hard plastic, and a flexible support made of silicone rubber. This patent discloses a system in which the relative stiffness of the cannula is at least 10 or 100 times the stiffness of the flexible support. Moreover, the patent is not primarily concerned with organic polymeric materials and, in fact, discloses a preference for metal cannulas and silicone rubber supports.

Clearly, it would be advantageous to provide a sleeve which is easy and relatively inexpensive to manufacture, is disposable, provides effective fluid seals and is able to maintain an open fluid path during surgery.

SUMMARY OF THE INVENTION

A new sleeve for use with surgical instruments particularly instruments useful to treat the eye, such as vitrectomy cutters, irrigation/aspiration instruments, emulsification instruments, illuminating instruments and the like, has been discovered. Substantial benefits are obtained with a sleeve made of one or more organic polymeric materials. For example, both effective fluid seals and an unobstructed, preferably substantially noncollapsible, fluid flow path are obtained during use of the present sleeves.

This sleeve, preferably made primarily of one or more organic polymeric materials, provides effective fluid seals while being easier and less costly to produce relative to the prior art metal sleeves. For example, the present sleeves may be suitable for being mass produced as opposed to the metal sleeves, which often require custom fitting to one particular surgical instrument. Thus, the relatively large compliance of the present sleeve allows effective fluid seals to be obtained without requiring the degree of customization needed when using metal sleeves.

As noted above, sleeves have previously been made of silicone polymers. The present sleeves advantageously have a reduced tendency to collapse relative to such silicone polymer sleeves. This feature makes the present sleeves more effective relative to the silicone polymer sleeves. For example, the present sleeves have a reduced tendency to collapse around the instrument during use, and therefore, are more effective in providing an open and unobstructed flow path for irrigation fluid and/or other fluid during the surgical procedure. In addition, the present sleeves preferably have a reduced tendency, relative to silicone sleeves to hang up on the edge of the surgical incision. Further, the present sleeves can be constructed to be relatively thin and tapered at the distal end to provide for increased ease in inserting the instrument and sleeve into the surgical incision.

The sleeves of the present invention include an elongated sleeve portion and a hub secured to, i.e., bonded to, affixed to or one integral component with, the sleeve portion. The sleeve portion has a hollow interior space into which the distal end portion of the surgical instrument is placed and through which fluid, e.g., such as irrigation fluid and the like, is passed. At least one fluid outlet is provided at or near the distal end portion of the sleeve portion to allow fluid to leave the interior space. The sleeve portion also has an opening at or near its distal end through which the distal end portion of the instrument extends. The fluid outlet or outlets are preferably placed away from this opening in the sleeve portion. Preferably, the sleeve portion forms a substantially fluid-tight seal to substantially prevent fluid in the interior space of the sleeve portion from passing through this opening when the distal end portion of the instrument extends through the opening.

The hub, which is secured to the sleeve portion, is sized and adapted to receive at least a portion of the surgical instrument. The hub includes at least one substantially fluid-tight seal adapted to substantially prevent fluid in the hub from passing out of the hub through the opening in the hub at which the instrument enters the hub. In one embodiment, the hub preferably further includes a fluid inlet adapted to supply fluid to the interior space of the sleeve portion.

The present infusion sleeve is made from one or more organic, i.e., carbon-based, polymeric materials. Such organic polymeric materials are different from silicone polymers or rubbers. Such sleeves preferably comprise a major amount, i.e., 50% by weight or more, of such organic polymeric materials and more preferably are made substantially completely of such organic polymeric materials. Further, the present sleeves are substantially metal-free, i.e., substantially-free of metals other than relatively minor amounts of metallic components which may be present, e.g., as polymerization catalysts, additives and the like, in the organic polymeric materials. Also, the presently useful organic polymeric materials are substantially free of silicon.

The presently useful organic polymeric materials preferably have at least one of certain properties which aid in the functioning of the present system. In one embodiment, the organic polymeric material preferably has a Shore D Hardness of about 90 or less, more preferably about 70 or less. Such materials are relatively flexible and compliant. In one embodiment, the sleeve portion is harder than the hub. Preferably, the sleeve is less than 10 times as hard as the hub and more preferably, the sleeve is less than about 5 times as hard, based on the Shore D scale, as the hub. Of course, the material used in the elongated sleeve portion should be capable of being fabricated into a hollow tube of the size and surface quality suitable for use in an infusion sleeve. In this regard, the sleeve portion preferably has a substantially smooth exterior surface so as to avoid any undue irritation to the eye being surgically treated. More preferably, organic polymeric materials used in the present system are (1) sufficiently flexible and compliant to form the requisite fluid-tight seal or seals; (2) sufficiently rigid so that the fluid path internal to the sleeve portion is substantially non-collapsible in normal use; and (3) such that the exterior surface of the sleeve portion is substantially smooth so as to avoid undue irritation or other damage to the eye being surgically treated.

Among the organic polymeric materials useful in the present invention include various elastomers, thermoplastics, plasticized thermoplastics and mixtures thereof. Of course, the particular organic polymeric material or materials used should have no undue adverse effect on the surgical instrument, the irrigation fluid or other fluid being carried by the sleeve, and, most importantly, on the eye being operated on. Examples of suitable organic polymeric materials include polyurethanes, preferably thermoplastic polyurethanes, polyesters, acrylonitrile-butadiene-styrene copolymers, polyolefins, plasticized polyvinyl chloride and mixtures thereof. A particularly useful class of organic polymeric materials are the thermoplastic polyurethanes.

Polyurethane polymers are normally addition products between one or more diisocyanates and one or more dihydroxyl or trihydroxyl functional compounds. A diisocyanate is a compound having two functional isocyanate groups. At least one hydroxyl-containing compound preferably is a difunctional macromolecular glycol.

Any suitable diisocyanate may be utilized in preparing the presently useful polyurethanes. The diisocyanate is preferably non-aromatic. Examples of useful diisocyanates include aliphatic organic diisocyanates such as bicyclohexyl methane-4, 4'-diisocyanate, hexamethylene diisocyanate, isophorone diisocyanate, trimethyl hexamethylene diisocyanate, dimer acid diisocyanate and the like. A particularly useful diisocyanate is bicyclohexyl methane-4,4'-diisocyanate.

Any suitable difunctional polyol or mixture of such polyols may be utilized in preparing the presently useful polyurethanes. In one embodiment, the polyol is preferably polytetramethylene ether glycol having the following formula:

$$H\text{-}(O\text{-}CH_2\text{—}CH_2\text{—}CH_2\text{—}CH_2)_n\text{-}OH$$

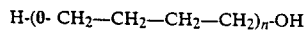

where n is chosen so that the average molecular weight of the glycol is in the range of about 500 to about 5000, more preferably about 1000 to about 3000, and especially about 2000.

Other polyols may be utilized in producing the presently useful polyurethane-type polymers. For example, low molecular weight glycols are useful as chain extenders. The low molecular weight glycol preferably has a molecular weight in the range of about 60 to about 300. Examples include ethylene glycol, diethylene glycol, propylene glycol, dipropylene glycol, neopentyl glycol, cyclohexane himethanol, 1,4-butanediol and the like, with 1,4-butanediol being particularly preferred.

It is preferred that the polyurethane is not substantially cross-linked. That is, it is preferred that no cross-linking agent, such as a low molecular weight polyhydric (i.e., tri-hydric or higher) alcohol be added to the polymer mix.

The presently preferred thermoplastic polyurethanes may be prepared in any suitable manner, including various procedures conventionally utilized to produce thermoplastic polyurethanes.

Examples of the presently useful polyurethanes are medical-grade thermoplastic polyurethanes sold under the trademark Tecoflex by Thermedics of Woburn MA.

These are other aspects and advantages of the present invention are set forth in the following detailed description and claims, particularly when considered in conjunction with the accompanying drawings in which like parts bear like reference numerals.

DETAILED DESCRIPTION OF THE DRAWINGS

Figure 1:
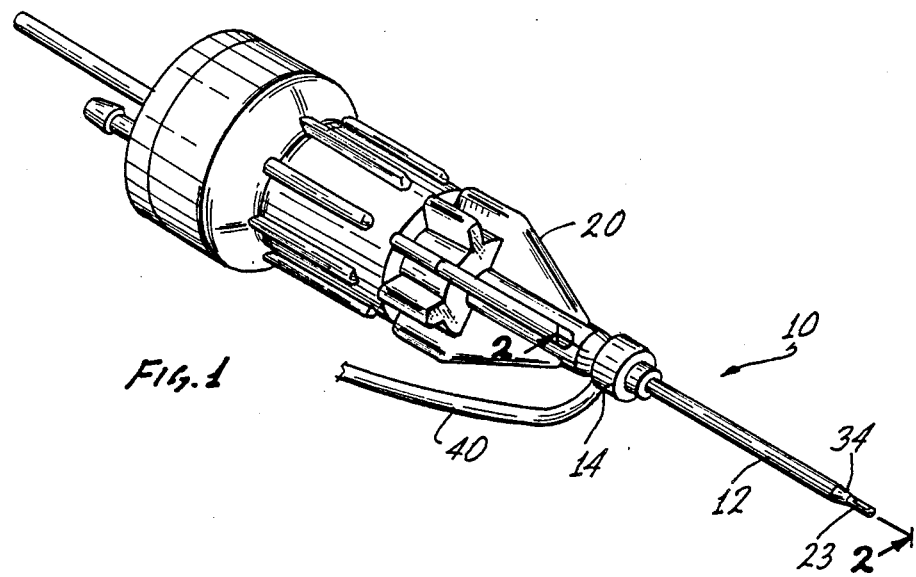
FIG. 1 is a front-side view, in perspective, of one embodiment of the present infusion sleeve shown in use with a vitrectomy cutter.
Figure 2:
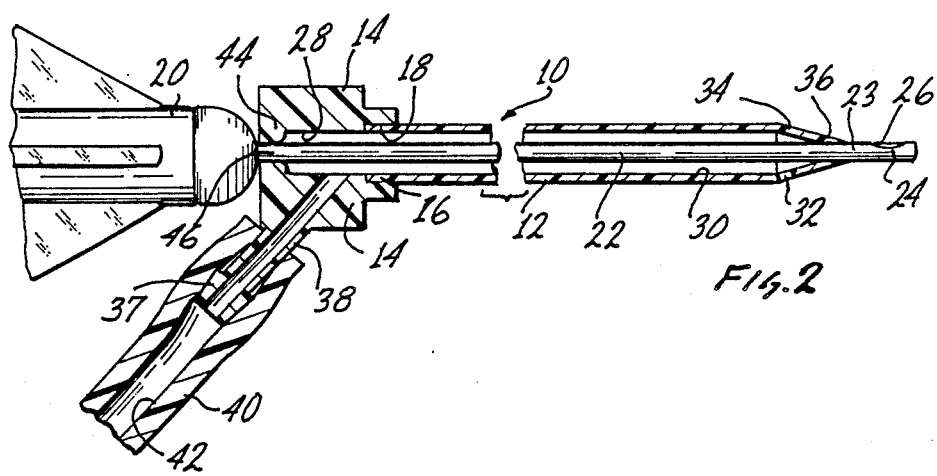
FIG. 2 is a partial cross-sectional view taken along line 2—2 of FIG. 1.

Referring now to FIGS. 1 and 2, an infusion sleeve, shown generally at 10, includes an elongated, hollow tube 12 and a hub 14. Infusion sleeve 10 is made of thermoplastic polyurethane, with tube 12 having a Shore D hardness of 60, and hub 14 having a Shore D hardness of 60. Both tube 12 and hub 14 are made of polyurethane similar to that sold by Thermedics under the trademark Tecoflex.

Tube 12 is sized so that its proximal end portion 16 matingly fits into annular opening 18 of hub 14. Proximal end portion 16 is solvent (such as cyclohexanone and the like) bonded into annular opening 18. In this manner tube 12 is secured to hub 14. Of course, tube 12 can be secured to hub 14 in various other, e.g., conventional, ways such as through the use of adhesives, heat and the like. Alternately, if desired, tue 12 and hub 14 can be made as one integral component.

A vitrectomy cutter 20 includes an elongated, hollow needle 22 which, in turn, has an opening 24 at the distal end 23 thereof. A blade 26 can be seen in hole 24 and i capable of being activated to cut the vitreous material during the vitrectomy.

Hollow needle 22 extends through the hollow opening 28 of hub 14 and through the hollow opening 30 (which is coaxial with opening 28) of tube 12. The distal end portion 23 of needle 22 extends out of hollow tube 12.

Hollow tube 12 includes a fluid outlet 32 which is located in the distal end section 34 of hollow tube 12. Distal end section 34 is tapered relative to the remainder of hollow tube 12 and acts to form a substantially fluid tight seal 36 around needle 22.

Hub 14 is molded to include a fluid inlet 37 which includes a flow passage 38 which, in turn, is in fluid communication with hollow opening 28. A plastic tubing 40, including flow channel 42, is fitted onto fluid inlet 37. A inwardly extending projection 44 is included in hub 14 and acts to form a substantially fluid-tight seal between hub 14 and the proximal end portion 46 of needle 22.

Infusion sleeve 10 functions as follows. When vitrectomy cutter 20 is to be used, tubing 40 is connected to a source of irrigation fluid, and needle 22 is placed in and through sleeve 10 so as to be located as shown in FIGS. 1 and 2. A substantial portion of the needle 22 and sleeve 10 are inserted through an incision into the eye being treated. As vitrectomy cutter 20 cuts into the vitreous tissue, irrigation fluid is made to flow from the fluid source (not shown) through the flow channel 42, the flow passage 38, hollow opening 28, hollow opening 30 and fluid outlet 32 to provide irrigation fluid to the operative site.

After the desired cutting has taken place, the flow of irrigation fluid is stopped, the needle 22 and sleeve 10 are withdrawn from the eye and the incision in the eye is closed. Infusion sleeve 10 is separated from vitrectomy cutter 20. Although it may be possible to sanitize or sterilize infusion sleeve 10 so that it can be reused, e.g., in the treatment of another patient, it is preferred that infusion sleeve 10 be disposed of after a single use. This is one advantage of the present infusion sleeves, which are made of organic polymeric material, relative to the previously used metal sleeves. The present infusion sleeves can be produced by mass production techniques, relatively inexpensively as compared to the prior metal sleeves which involved expensive precision manufacturing and were used repeatedly.

In addition the present infusion sleeves, such as infusion sleeve 10, preferably have a very desirable combination of properties. For example, infusion sleeve 10 is sufficiently compliant so that substantially fluid tight seals are obtained and maintained at seal 36 and at the place where projection 44 contacts needle 22. Further, tube 12 is sufficiently rigid so as not to collapse during use. This allows hollow opening 28 to remain unobstructed so that a supply of irrigation fluid can pass through hollow openings 28 and 30 and outlet 32. Still further, the outside surface of tube 12 is substantially smooth so as not to cause any undue irritation and/or other damage to the eye as tube 12 is inserted into and withdrawn from the eye. In contrast, prior sleeves made of silicone polymer tend to be tacky and can cause chafing.

Figure 3:
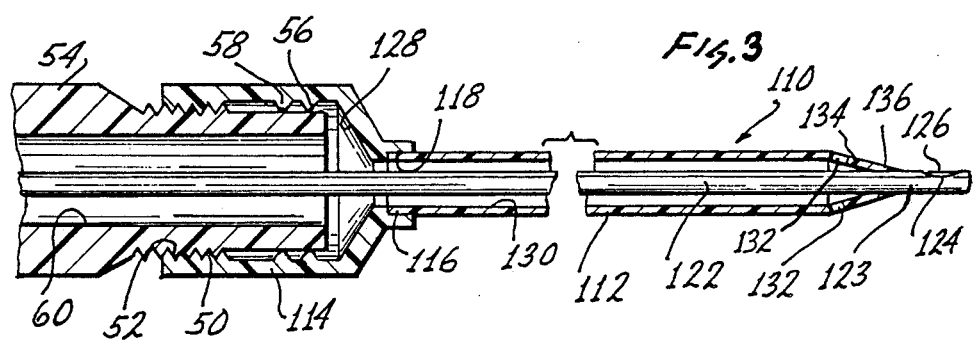
FIG. 3 is a side elevational view, partially in cross-section, showing another embodiment of the present infusion sleeve in use with a vitrectomy cutter.

FIG. 3 illustrates another embodiment of the present invention. This infusion sleeve, shown generally at 110, is made of a substantially similar thermoplastic polyurethane material as is infusion sleeve 10. Components of infusion sleeve 110 which correspond to components of infusion sleeve 10 are indicated by corresponding reference numerals increased by 100. Tube 112 has a shore D hardness of 60 and hub 114 has a shore D hardness of 29. Tube 112 is harder than hub 114 thouqh it is less than about 5 times, based on the relative shore D hardnesses as hard. Except as expressly stated herein, infusion sleeve 110 is structured and functions in a manner similar to infusion sleeve 10.

A primary difference, in addition to that noted above, between infusion sleeve 110 and infusion sleeve 10 is in the structure of hub 114. This component is internally threaded at its proximal end, which threads 50 matingly engage the external threads 52 of vitrectomy cutter 54. Two inwardly extending, circumferential projections 56 and 58 are located on hub 114 and contact cutter 54 to form fluid tight seals between hub 114 and cutter 54. In addition, hub 114 does not have a fluid inlet. Irrigation fluid is provided to hollow opening 128 by passage 60 which is located within cutter 54 and is in fluid communication with an irrigation fluid source (not shown). Further, infusion sleeve 110 includes two fluid outlets 132 located substantially opposite each other in the distal end section 134 of tube 112.

When it is desired to use infusion sleeve 110, it is simply threaded onto the distal end of cutter 54 so that needle 122 extends through and out of tube 112, as shown in FIG. 3. After use, infusion sleeve 110 is unthreaded from cutter 54 and discarded. Substantially all of the advantages discussed previously with regard to infusion sleeve 10 are also obtained with infusion sleeve 110.

Figure 4:
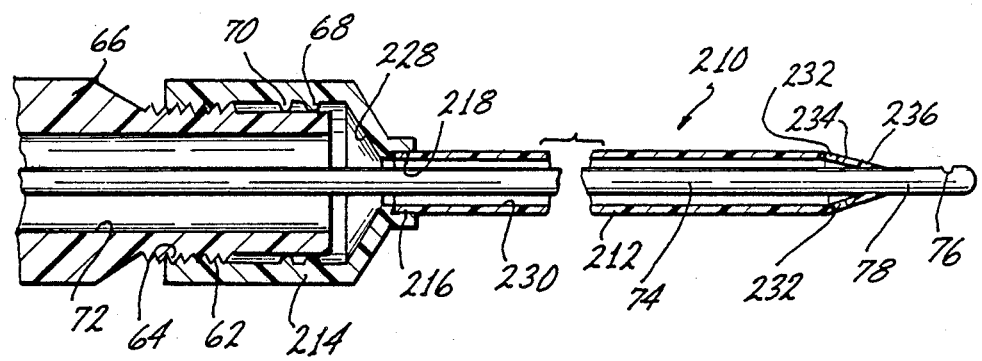
FIG. 4 is a side elevational view, partially in cross-section, showing a further embodiment of the present infusion sleeve, in use with an irrigation/aspiration instrument.

FIG. 4 illustrates a further embodiment of the present invention. This infusion sleeve, shown generally at 210, is made of the same thermoplastic polyurethane materials as is infusion sleeve 110. Components of infusion sleeve 210 which correspond to components of infusion sleeve 10 are indicated by corresponding reference numerals increased by 200. Except as expressly stated herein, infusion sleeve 210 is structured and functions in a manner similar to infusion sleeve 10.

The primary differences between infusion sleeve 210 and infusion sleeve 10 are (1) infusion sleeve 210 is to be used with an irrigation/aspiration instrument, while infusion sleeve 10 is for use with a vitrectomy cutter, (2) in the structure of hub 214, and (3) infusion sleeve 210 has two, mutually opposing fluid outlets 232. The structure of infusion sleeve 210 is very similar to that of infusion sleeve 110.

Hub 214 is internally threaded at its proximal end, which threads 62 matingly engage the external threads 64 of an irrigation/aspiration instrument 64 of an irrigation/aspiration instrument 66. Two inwardly extending, circumferential projections 68 and 70 are located on hub 214 and contact instrument 66 to form fluid tight seals between hub 214 and instrument 66. In addition hub 214 does not have a fluid outlet. Irrigation fluid is provided to follow opening 228 by passage 72 which is located within instrument 66 and is in fluid communication with an irrigation fluid source (not shown).

When it is desired to use infusion sleeve 210, it is simply threaded onto the distal end of instrument 66 so that an elongated needle 74 of instrument 66 extends through and out of tube 212, as shown in FIG. 4. Elongated needle 74 is hollow and has an opening 76 at its distal end 78. Irrigation/aspiration instrument 66 is positioned so that the distal end 78 of elongated needle 74 is at the desired location within the eye. Irrigation fluid is provided through passage 72, hollow opening 228, hollow opening 230 and fluid outlets 232 to the desired location within the eye. A vacuum is drawn by instrument 66 on the interior hollow space within needle 74. This vacuum causes tissue from the eye plus irrigation fluid to be aspirated through opening 76 and elongated needle 74 back to instrument 66. After the desired amount of material has been aspirated, instrument 66 is withdrawn from the eye. After use, infusion sleeve 210 is unthreaded from instrument 66 and discarded. Substantially all the advantages discusses previously with regard to infusion sleeves 10 and 110 are also obtained with infusion sleeve 210.

Figure 5:
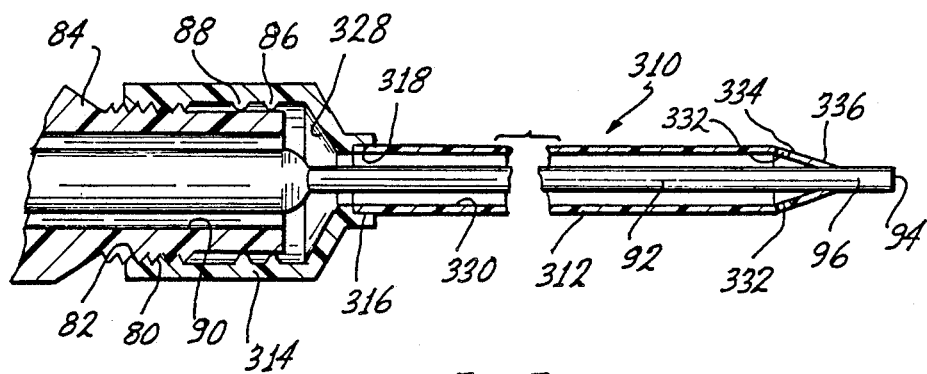
FIG. 5 is a side elevation view, partially in cross-section, showing yet another embodiment of the present infusion sleeve, in use with an emulsification instrument.

FIG. 5 illustrates a further embodiment of the present invention. This infusion sleeve, shown generally at 310, is made of the same thermoplastic polyurethane materials as is infusion sleeve 110. Components of infusion sleeve 310 which correspond to components of infusion sleeve 10 are indicated by corresponding reference numerals increased by 300. Except as expressly stated herein, infusion sleeve 310 is structured and functions in a manner similar to infusion sleeve 10.

The primary differences between infusion sleeve 210 and infusion sleeve 10 are (1) infusion sleeve 310 is to be used with an emulsification instrument, e.g., a phaco emulsification instrument, while infusion sleeve 10 is for use with a vitrectomy cutter, (2) in the structure of hub 314, and (3) infusion sleeve 310 has two mutually opposing fluid outlets 232. The structure on infusion sleeve 310 is very similar to that of infusion sleeve 110.

Hub 314 is internally threaded at its proximal end, which threads 80 matingly engage the external threads 82 of an emulsification instrument 84. Two inwardly extending, circumferential projections 86 and 88 are located on hub 314 and contact instrument 84 to form fluid tight seals between hub 314 and instrument 84. In addition hub 314 does not have a fluid outlet. Irrigation fluid is provided to hollow opening 228 by passage 90 which is located within instrument 84 and is in fluid communication with an irrigation fluid source (not shown).

When it is desired to use infusion sleeve 310, it is simply threaded onto the distal end of instrument 84 so that a pulsating needle 92 of instrument 84 extends through and out of tube 312, as shown in FIG. 4. Pulsating needle 92 is hollow and has an opening 94 at its distal end 96. Emulsification instrument 84 is positioned so that the distal end 96 of pulsating needle 74 is at the desired location within the eye. Irrigation fluid is provided through passage 90, hollow opening 328, hollow opening 330 and fluid outlets 332 to the desired location within the eye.

Pulsating needle 92 is caused to pulsate axially at a rate on the order of 40,000 cycles per second. This action causes tissue within the eye to fragment.

A vacuum is drawn by instrument 66 on the interior hollow space within needle 74. This vacuum causes the fragmented tissue from the eye plus irrigation fluid to be aspirated through opening 94 and pulsating needle 92 back to instrument 84. After the desired amount of material has been aspirated, instrument 84 is withdrawn from the eye. After use, infusion sleeve 310 is unthreaded from instrument 84 and discarded. Substantially all the advantages discusses previously with regard to infusion sleeves, 10 and 110 are also obtained with infusion sleeve 310. In addition, infusion sleeve 310 is able to effectively provide a fluid tight seal at seal 336 despite the rapid back and forth movements, i.e., the pulsations, of pulsating elongated needle 92. Such a fluid tight seal would be difficult, if not impossible, to achieve with a metal tube in place of polyurethane tube 312. Such metal tube would be subject to galling. In addition, metal particles might be formed and lodge in the eye, causing distress and possible sight damage. The present polyurethane tube 312 avoids these problems.

Infusion sleeves in accordance with the present invention for use with irrigation/aspiration instruments and emulsification instruments can be structured in a manner substantially similar to that of infusion sleeve 10. That is, for example, such infusion sleeves can be structured to have a fluid inlet and a flow passage similar to infusion sleeve 10. Such infusion sleeves are within the scope of the present invention.

Of course, it is clear that the infusion sleeve of the present invention may have other structures to suit the particular application involved. In any event, substantial advantages, e.g., sufficient compliance, rigidity and smoothness, are achieved with the present infusion sleeves made of organic polymeric material.

While this invention has been described with respect to various specific examples and embodiments, it is to be understood that the invention is not limited thereto and that it can be variously practiced within the scope of the following claims.

What is claimed is:

1. A sleeve useful on a surgical instrument comprising: an elongated sleeve portion having a hollow interior space through which fluid is passed, and at least one fluid outlet at or near the distal end portion of said elongated sleeve portion to allow fluid to leave said interior space; and a hub secured to said elongated sleeve portion and adapted to receive at least a portion of said surgical instrument, said hub including one or more surfaces structured and adapted to contact said surgical instrument so as to substantially prevent fluid in said hub from passing out of said hub through the opening in said hub through which said surgical instrument enters said hub, said elongated sleeve portion and said hub each being made of one or more organic polymeric materials substantially free of silicon, and said elongated sleeve portion being harder than said hub.

2. The sleeve of claim 1 wherein said elongated sleeve portion and said hub each have a hardness of about 90 Shore Hardness D or less.

3. The sleeve of claim 1 wherein said elongated sleeve portion has a hardness of about 70 Shore Hardness D or less.

4. The sleeve of claim 1 wherein said elongated sleeve portion is flexible at normal use conditions.

5. The sleeve of claim 1 wherein said elongated sleeve is less than 10 times as hard as said hub.

6. The sleeve of claim 1 wherein said elongated sleeve is less than 5 times, based on relative Shore D values, as hard as said hub.

7. The sleeve of claim 1 wherein said organic polymeric materials are selected from the group consisting of elastomers, thermoplastics, plasticized thermoplastics and mixtures thereof.

8. The sleeve of claim 1 wherein said organic polymeric materials are selected from the group consisting of polyurethanes, polyesters, acrylonitrile-butadienestyrene copolymers, polyolefins, plasticized polyvinyl chloride and mixtures thereof.

9. The sleeve of claim wherein said organic polymeric materials are selected from the group consisting of thermoplastic polyurethanes and mixtures thereof.

10. The sleeve of claim 11 wherein said thermoplastic polyurethanes are derived from one or more non-aromatic diisocyanates.

11. The sleeve of claim 1 wherein said elongated sleeve portion further includes an outlet through which the distal end portion of said surgical instrument extends out of said interior space, said outlet being structured to substantially prevent fluid from said interior space from passing out of said interior space between said outlet and said surgical instrument.

12. The sleeve of claim 1 wherein said hub further includes a fluid inlet adapted to supply fluid to said interior space.

13. The sleeve of claim 1 wherein said elongated sleeve portion and said hub are separate parts and are bonded together.

14. The sleeve of claim 1 wherein said elongated sleeve portion and said hub are made of substantially the same organic polymeric material.

15. The infusion sleeve of claim 1 wherein said elongated sleeve portion is substantially non-collapsible at normal use conditions.

16. The infusion sleeve of claim 1 wherein said elongated sleeve portion has a substantially smooth outer surface which is substantially non-irritating.

17. An apparatus comprising:
a surgical instrument useful for treating the eye of a patient; and
a sleeve comprising an elongated sleeve portion having a hollow interior space through which fluid is passed, and at least one fluid outlet at or near the distal end portion of said elongated sleeve portion to allow fluid to leave said interior space, and a hub secured to said elongated sleeve portion and adapted to receive at least a portion of said surgical instrument, said hub including one or more surfaces structured and adapted to contact said surgical instrument so as to substantially prevent fluid in said hub from passing out of said hub through the opening in said hub through which said surgical instrument enters said hub, said elongated sleeve portion and said hub each being made of one or more organic polymeric materials substantially free of silicon, and said elongated sleeve portion being harder than said hub.

18. The apparatus of claim 17 wherein said surgical instrument is a vitrectomy cutter.

19. The apparatus of claim 17 wherein said surgical instrument is a surgical irrigation/aspiration instrument.

20. The apparatus of claim 17 wherein said surgical instrument is an emulsification instrument.

21. A sleeve useful on a surgical instrument comprising: an elongated sleeve portion having a hollow interior space through which fluid is passed, and at least one fluid outlet at or near the distal end portion of said elongated sleeve portion to allow fluid to leave said interior space; and a hub secured to said elongated sleeve portion and adapted to receive at least a portion of said surgical instrument, said hub including one or more surfaces structure and adapted to contact said surgical instrument so as to substantially prevent fluid in said hub from passing out of said hub through the opening in said hub through which said surgical instrument enters said hub, said elongated sleeve portion and said hub each being made of one or more organic polymeric materials, said organic polymeric materials being selected from the group consisting of thermoplastic polyurethane and mixtures thereof.

22. The sleeve of claim 21 wherein said thermoplastic polyurethanes are derived from one or more nonaromatic diisocyanates.

23. The sleeve of claim 21 wherein said elongated sleeve portion is flexible at normal use conditions.

24. The sleeve of claim 21 wherein said elongated sleeve portion further includes an outlet through which the distal end portion of said surgical instrument extends out of said interior space, said outlet being structured to substantially prevent fluid from said interior space from passing out of said interior space between said outlet and said surgical instrument.

25. The sleeve of claim 21 wherein said hub further includes a fluid inlet adapted to supply fluid to said interior space.

26. The sleeve of claim 21 wherein said elongated sleeve portion and said hub are separate parts and are bonded together.

27. The sleeve of claim 21 wherein said elongated sleeve portion is substantially non-collapsible at normal use conditions.

28. The sleeve of claim 21 wherein said elongated sleeve portion has a substantially smooth outer surface which is substantially non-irritating.

29. An apparatus comprising:
a surgical instrument useful for treating the eye of a patient; and
a sleeve comprising an elongated sleeve portion having a hollow interior space through which fluid is passed, and at least one fluid outlet at or near the distal end portion of said elongated sleeve portion to allow fluid to leave said interior space, and a hub secured to said elongated sleeve portion and adapted to receive at least a portion of said surgical instrument, said hub including one or more surfaces structured and adapted to contact said surgical instrument so as to substantially prevent fluid in said hub from passing out of said hub through the opening in said hub through which said surgical instrument enters said hub, said elongated sleeve portion and said hub each being made of one or more organic polymeric materials, said organic polymeric materials being selected from the group consisting of thermoplastic polyurethanes and mixtures thereof.

30. The apparatus of claim 29 wherein said surgical instrument is a vitrectomy cutter.

31. The apparatus of claim 29 wherein said surgical instrument is a surgical irrigation/aspiration instrument.

32. The apparatus of claim 29 wherein said surgical instrument is an emulsification instrument.

* * * * *

UNITED STATES PATENT AND TRADEMARK OFFICE
CERTIFICATE OF CORRECTION

PATENT NO. : 4,897,079
DATED : Jan. 30, 1990
INVENTOR(S) : Zaleski et al It is certified that error appears in the above-identified patent and that said Letters Patent is hereby corrected as shown below:

In the Abstract - next to the last line change "non-irrigating" to -- non-irritating --.

Column 4, line 65 change "tue" to -- tube --.

Column 5, line 1 change "i" to -- is --.

Column 6, line 5 change "thouqh" to -- though --.

Column 8, line 66 change "claim wherein" to -- claim 1 wherein --.

Column 9, line 1 change "claim 11" to -- claim 9 --.

Column 9, line 60 change "structure" to -- structured --.

Signed and Sealed this

Eleventh Day of June, 1991

*Attest:*

HARRY F. MANBECK, JR.

*Attesting Officer*   *Commissioner of Patents and Trademarks*